US008389211B2

(12) United States Patent
Harada et al.

(10) Patent No.: US 8,389,211 B2
(45) Date of Patent: Mar. 5, 2013

(54) METHOD FOR DETERMINATION OF TARGET SUBSTANCE

(75) Inventors: Tomoko Harada, Kanagawa (JP); Yuuki Watanabe, Kanagawa (JP)

(73) Assignee: Sony Corporation, Tokyo (JP)

( * ) Notice: Subject to any disclaimer, the term of this patent is extended or adjusted under 35 U.S.C. 154(b) by 80 days.

(21) Appl. No.: 12/867,447

(22) PCT Filed: Feb. 27, 2009

(86) PCT No.: PCT/JP2009/053740
§ 371 (c)(1),
(2), (4) Date: Aug. 12, 2010

(87) PCT Pub. No.: WO2009/107803
PCT Pub. Date: Sep. 3, 2009

(65) Prior Publication Data
US 2010/0317128 A1  Dec. 16, 2010

(30) Foreign Application Priority Data
Feb. 27, 2008  (JP) ................................ P2008-046769

(51) Int. Cl.
*C12Q 1/68*  (2006.01)
(52) U.S. Cl. .............................. 435/6; 435/325; 435/375
(58) Field of Classification Search ........................ None
See application file for complete search history.

(56) References Cited

U.S. PATENT DOCUMENTS

| 7,892,734 | B2 * | 2/2011 | Lu et al. ........................ 435/6.11 |
| 8,071,734 | B2 * | 12/2011 | Stanton et al. ................. 536/22.1 |
| 2003/0170650 | A1 * | 9/2003 | Karube et al. ....................... 435/6 |
| 2005/0100919 | A1 * | 5/2005 | Stanton et al. ..................... 435/6 |
| 2006/0088864 | A1 * | 4/2006 | Smolke et al. ..................... 435/6 |
| 2006/0194240 | A1 * | 8/2006 | Arnold et al. ...................... 435/6 |
| 2007/0037171 | A1 * | 2/2007 | Lu et al. ............................ 435/6 |
| 2008/0269258 | A1 * | 10/2008 | Breaker et al. .............. 514/263.3 |

FOREIGN PATENT DOCUMENTS

| EP | 1992705 A1 | 11/2008 |
| JP | 07-298897 | 11/1995 |
| JP | 2005-031066 | 2/2005 |
| JP | 2005-508495 | 3/2005 |
| WO | 03/062442 A1 | 7/2003 |
| WO | 2008/009437 A2 | 1/2008 |

OTHER PUBLICATIONS

Centi et al., "Different approaches for the detection of thrombin by an electrochemical aptamer-based assay coupled to magnetic beads", Biosensors and Bioelectronics, 2008, pp. 1602-1609, vol. 23.
Morse, "Direct selection of RNA beacon aptamers", Biochemical and Biophysical Research Communications, 2007, pp. 94-101, vol. 359.
Fischer et al., "Aptasensors for biosecurity applications", Chemical Biology, 2007, pp. 316-328, vol. 11.
International Search Report dated Apr. 1, 2011 for corresponding European Patent Application No. 09715219.
International Search Report dated Mar. 19, 2009, for corresponding Patent Application PCT/JP2009/053740.
"Analytical Applications of Aptamers", Biosensors and Bioelectronics 20 (2005) pp. 2424-2434.
"An Electronic, Aptamer-Based Small-Molecule Sensor for the Rapid, Label-Free Detection of Cocaine in Adulterated Samples and Biological Fluids" J. Am. Chem. Soc., 2006, 128 (10), pp. 3138-3139.
"Screening Method of Endocrine Disrupting Chemicals Using a Surface Plasmon Resonance Sensor", Bunseki Kagaku vol. 51, No. 6, (2002) pp. 389-396.

* cited by examiner

*Primary Examiner* — Kimberly Chong
(74) *Attorney, Agent, or Firm* — K&L Gates LLP

(57) ABSTRACT

A method for highly sensitive determination of a target substance by means of an aptamer includes: causing an aptamer capable of specific binding with a target substance to bind competitively with said target substance and a nucleic acid strand having a base sequence complementary to at least a portion of said target substance, detecting at least either of the physical change and the chemical change that results from said aptamer binding with said nucleic acid strand, and determining said target substance based on the result of detection.

11 Claims, 11 Drawing Sheets

(1)

(2)

(1)

(2)

(a) 15 mer, 5 uL/min 480 sec (b) 10 mer, 10 uL/min 300 sec

LENGTH OF COMPLEMENTARY SEQUENCE : 15 mer

METHOD FOR DETERMINATION OF TARGET SUBSTANCE

CROSS REFERENCE TO RELATED APPLICATIONS

The present application is a National Stage of International Application No. PCT/JP2009/053740 filed on Feb. 27, 2009 and which claims priority to Japanese Patent Application No. 2008-046769 filed on Feb. 27, 2008, the entire contents of which are being incorporated herein by reference.

BACKGROUND

The present disclosure relates to a method for determination of molecules. More particularly, the present invention relates to a method for determination of molecules by means of an aptamer.

Biosensors consist of a material capable of discriminating molecules and a transducer to detect physical and/or chemical signals arising from mutual actions between the material and a target chemical substance. Among conventional materials capable of discriminating molecules are proteins such as enzymes, antibodies, and receptors.

Document 1 (BUNSEKI KAGAKU Vol. 51, No. 6, (2002) 389-396) discloses a method for high-speed screening of endocrine disrupting chemicals by means of a surface plasmon resonance (SPR) sensor. This method consists of immobilizing the hormone responsive sequence DNA (ERE) of the promoter region of the estrogen responsive gene on an SPR sensor chip and adding a purified estrogen receptor α (ER) to it, thereby measuring the mutual action of ER and ERE in real time without modification.

Unfortunately, proteins are unsuitable for long-term use because they are limited in life on account of their chemical and thermal instability and they are subject to nonspecific adsorption.

What is attracting attention as a substitute for proteins is an aptamer, which is a nucleic acid sequence that brings about a specific binding like an antibody for antigens ranging from low-molecular weight compounds to proteins. Being not a protein, an aptamer has an advantage in stability and life. Moreover, it is expected to find use as a biosensor because of its ability for reproduction under comparatively mild conditions, its potential for economical mass production by chemical synthesis, and its property characteristic of nucleic acids, such as reversible binding with and dissociation from complementary strands.

Document 2 (J. Am. Chem. Soc. 128, (2006) 3138-3139) discloses an electrochemical method for observing the change that occurs in the structure of an aptamer on account of the presence of cocaine as a target substance when the terminal of an aptamer is modified with methylene blue.

SUMMARY

Unfortunately, the method disclosed in Document 2 (J. Am. Chem. Soc. 128, (2006) 3138-3139) has the disadvantage of being unable to distinguish between the aptamer changing in structure due to its bonding with a target substance and the aptamer changing in structure due to its formation of double strands in its molecule (referred to as self-annealing hereinafter), which results in a higher noise level and hence a higher detection limit in proportion to the amount of the aptamer which has undergone self-annealing.

The present embodiments to provide a method for highly sensitive determination of a target substance by means of an aptamer.

According to the present embodiments, the above-mentioned technical problem is solved by the method for determination of a target substance which includes causing an aptamer capable of specific binding with a target substance to bind competitively with the target substance and a nucleic acid strand having a base sequence complementary to at least a portion of the aptamer, detecting at least either of the physical change and the chemical change that results from the aptamer binding with the nucleic acid strand, and determining the target substance based on the result of detection.

Incidentally, the target substance concerned with the present embodiments should be understood in a broad sense to include not only molecules but also ions. Also, "aptamer" denotes a DNA molecule or peptide that specifically binds with specific molecules.

According to the present embodiments, the aptamer should preferably be one which is immobilized on the detection surface of a sensor.

In this case, the sensor should preferably be one which performs detection based on the principle of surface plasmon resonance and which is capable of detecting the change in permittivity that results from the aptamer binding with the nucleic acid strand. Moreover, the sensor should preferably be one which performs detection based on the principle of quartz crystal microbalance and which is capable of detecting the change in mass that results from the aptamer binding with the nucleic acid strand.

According to an embodiment, the aptamer should preferably be one which has the stem loop structure and the nucleic acid strand should preferably be one which has a base sequence complementary to that of the non-stem portion of the aptamer. Having at least a base sequence complementary to that of the non-stem portion of the aptamer, the nucleic acid strand combines with the aptamer which has undergone self-annealing and unbinds the self-annealing of the aptamer.

Incidentally, the term "non-stem portion" used in the present invention denotes that portion of the aptamer that excludes the stem structure to form the complementary strand, and it denotes the loop portion having the loop structure and the bulge portion that does not form the complementary strand.

Moreover, according to an embodiment, the nucleic acid strand should preferably be one which has a base sequence non-complementary to the aptamer, or at least either of the aptamer and the nucleic acid strand should preferably be one which has a substituent to enhance at least either of the physical change and the chemical change resulting from the aptamer binding with the nucleic acid strand. The complementary strand constructed in this manner produces the desirable effect that the binding of the nucleic acid strand with the aptamer brings about significant physical and chemical changes for better detection sensitivity.

In addition, the nucleic acid strand may be one which is immobilized on the detection surface of the sensor.

In this case, the sensor performs detection based on the principle of surface plasmon resonance in such a way that the sensor detects the change in permittivity that results from the nucleic acid strand binding with the aptamer. Alternatively, the sensor performs detection based on the principle of quartz oscillator microbalance in such a way that the sensor detects the change in mass that results from the nucleic acid strand binding with the aptamer.

Finally, the present embodiments are concerned with a method for determination of a target substance in a sample, the method including the steps of: immobilizing on the detection surface an aptamer capable of specifically binding with the target substance; detecting at least either of the physical change and the chemical change which results from the aptamer binding with the nucleic acid strand, with the aptamer competitively binding with the target substance in the sample and the nucleic acid strand having a base sequence complementary to at least a portion of the aptamer; detecting at least either of the physical change and the chemical change which results from the aptamer binding with the nucleic acid strand, with the aptamer competitively binding with a prescribed amount of the target substance and a prescribed amount of the nucleic acid strand, thereby knowing the relationship between the amount of the target substance and the result of detection; and estimating the amount of the target substance in the sample.

Additional features and advantages are described herein, and will be apparent from, the following Detailed Description and the figures.

DETAILED DESCRIPTION

The following is the description of an embodiment with reference to the accompanying drawings.

Figure 1:
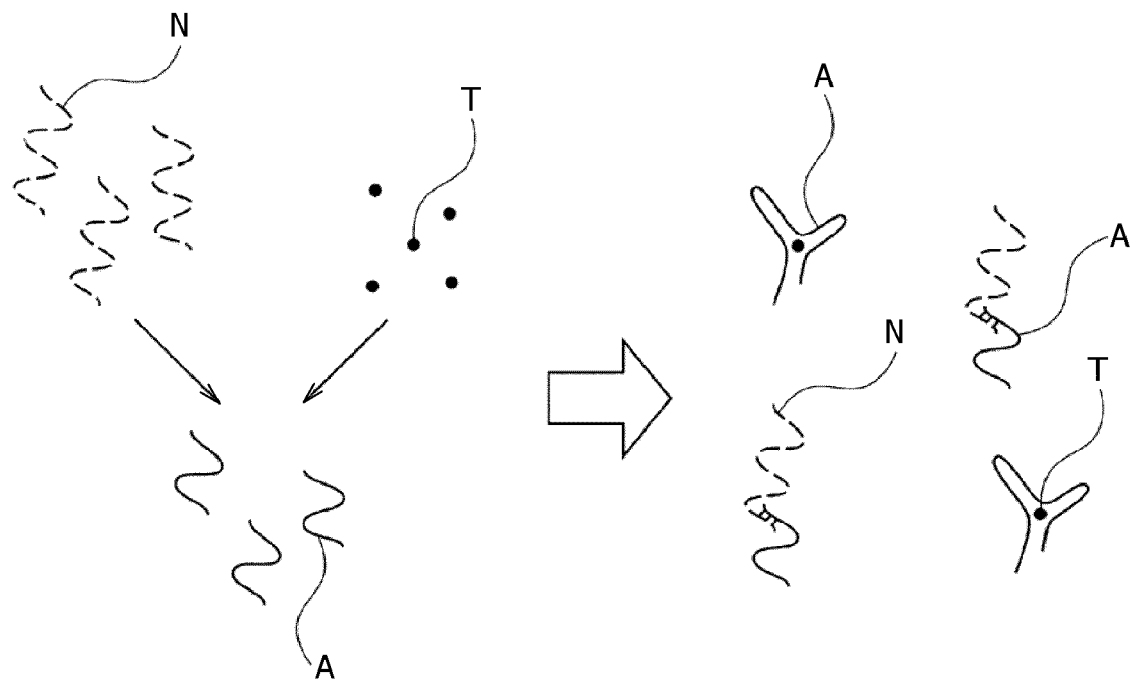
FIG. 1 is a schematic diagram illustrating the method pertaining to an embodiment.
Figure 1:
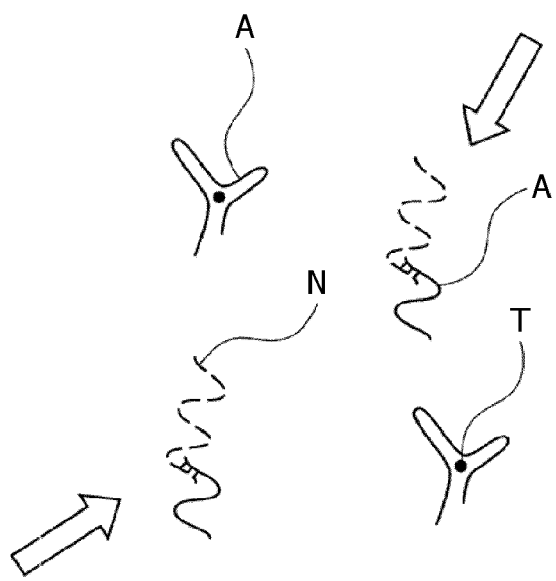

FIG. 1 is a schematic diagram illustrating the method for determination of a target substance according to the present embodiment. "T" denotes a target substance, "A" denotes an aptamer which specifically binds with the target substance, and "N" denotes a nucleic acid strand which has a base sequence complementary to at least a portion of the aptamer A.

The method according to the embodiment determines the target substance T by causing the aptamer A, which binds specifically with the target substance T, to bind competitively with the target substance T and the nucleic acid strand N which has a base sequence complementary to at least a portion of the aptamer A (see FIG. 1(1)). In this state, the binding of the aptamer A with the nucleic acid strand N brings about at least either the physical change and the chemical change to be detected (see FIG. 1(2)). The result of detection is used for determination of the target substance T.

The detection of at least either of the physical change and the chemical change that result from the aptamer A binding with the nucleic acid strand N offers the advantage of permitting the determination of the target substance T even in the case where, for example, the target substance T is a low-molecular weight one, which upon binding with the aptamer A, does not bring about at least either of the physical change and the chemical change that can be detected with a sufficiently high sensitivity.

In addition, the foregoing procedure excludes the effect produced by the self-annealing of the aptamer A. This leads to a reduction of noise due to the aptamer A which has undergone self-annealing.

Figure 2:
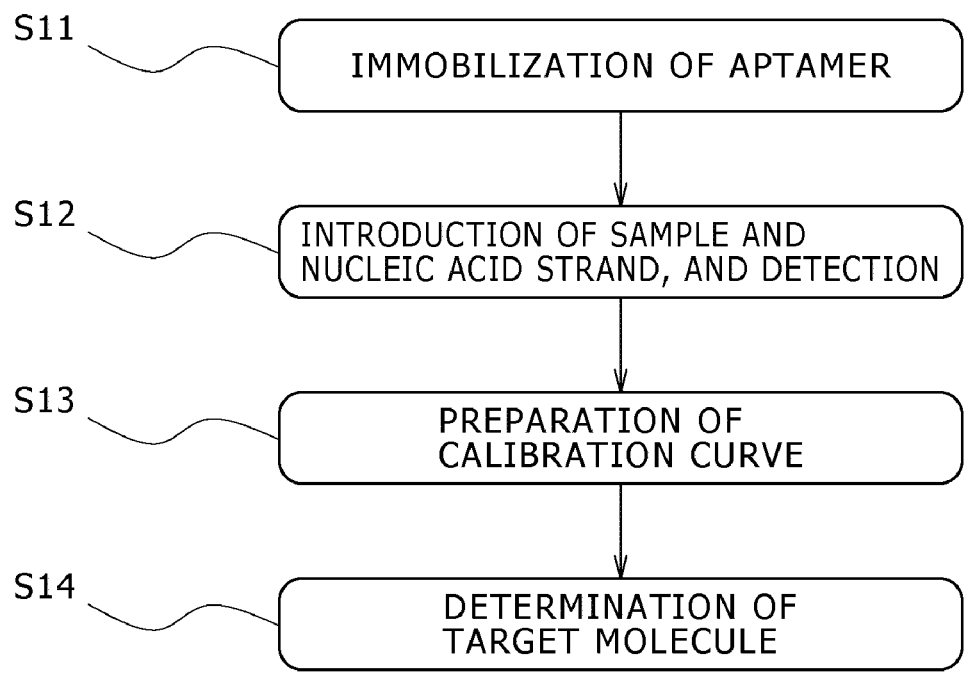
FIG. 2 is a flow chart for the first preferred embodiment of the method pertaining to the embodiment.
Figure 3:
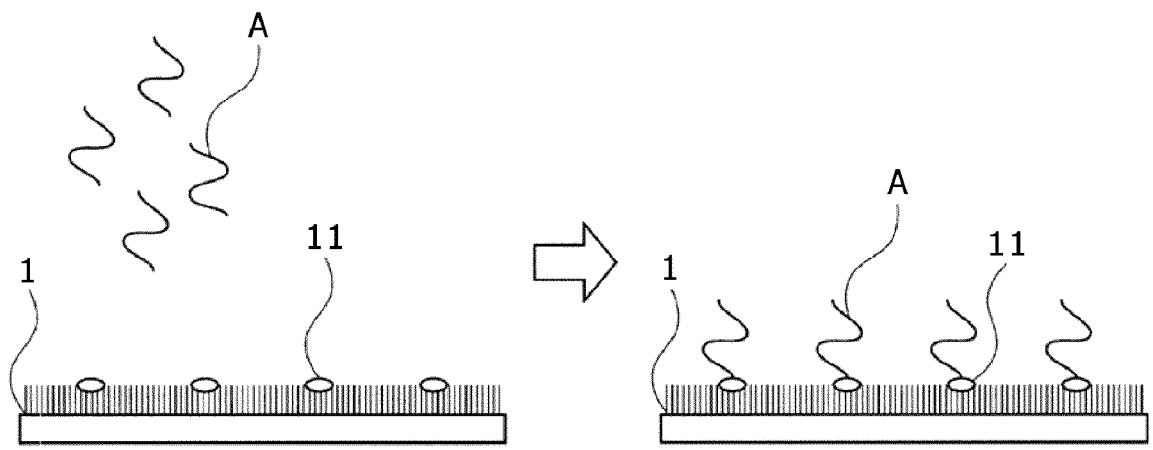
FIG. 3 is a schematic diagram illustrating the first step in the first preferred embodiment of the method pertaining to the embodiment.
Figure 4:
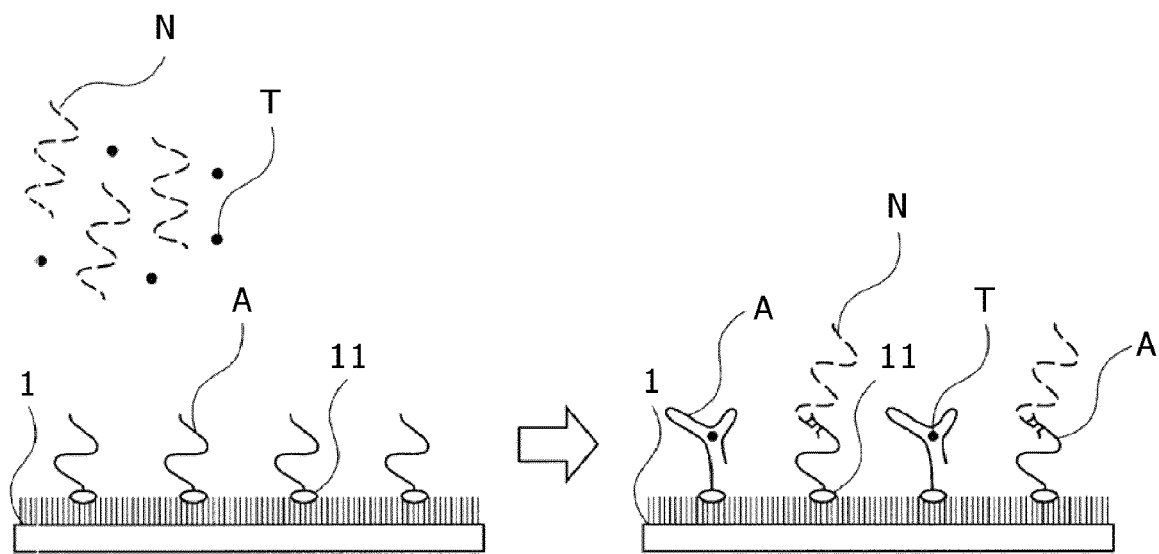
FIG. 4 is a schematic diagram illustrating the second step in the first preferred embodiment of the method pertaining to the embodiment.
Figure 4:
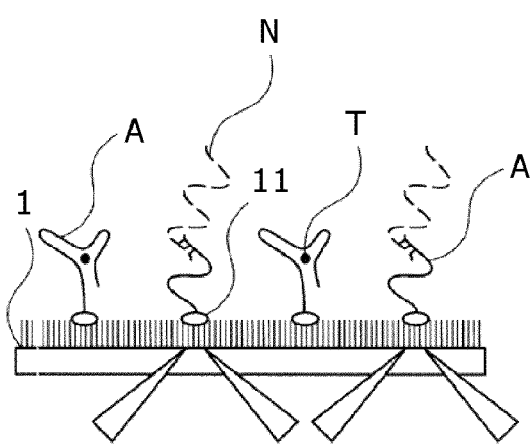
Figure 5:
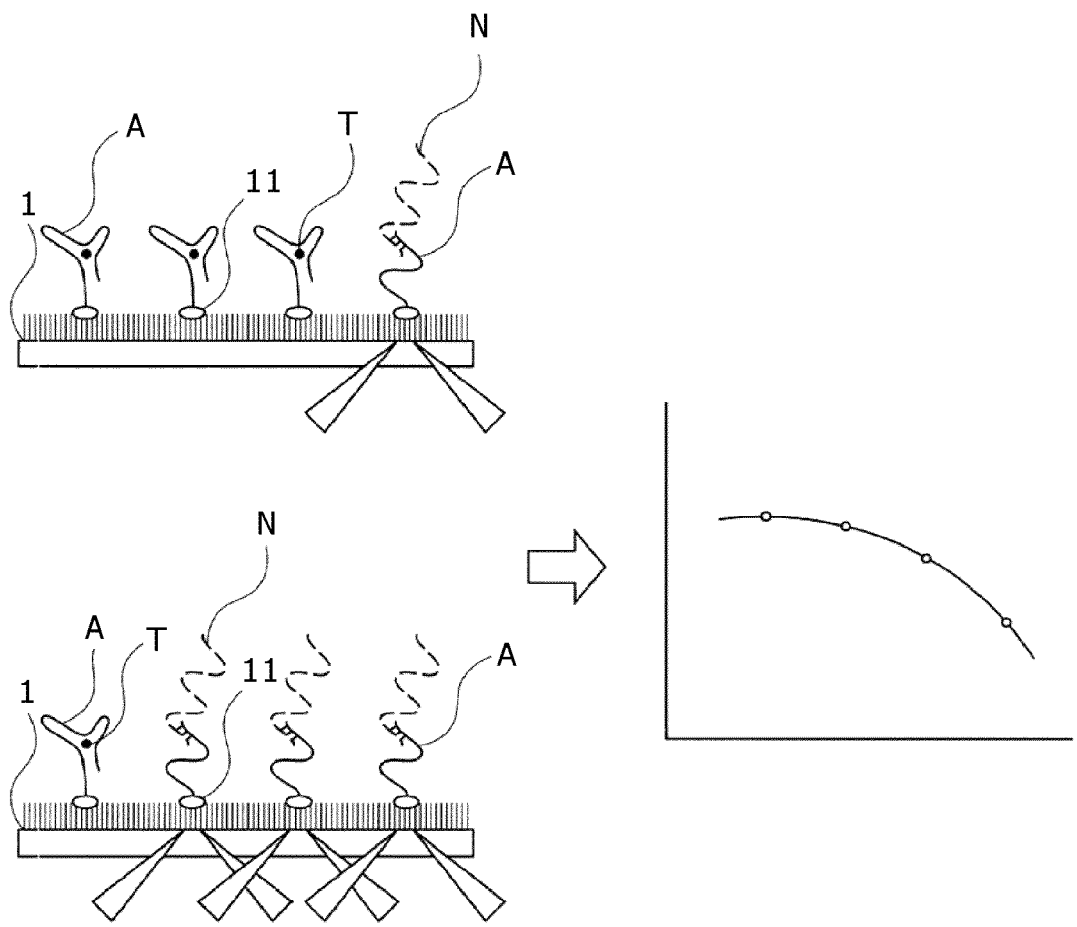
FIG. 5 is a schematic diagram illustrating the third step in the first preferred embodiment of the method pertaining to the embodiment.
Figure 6:
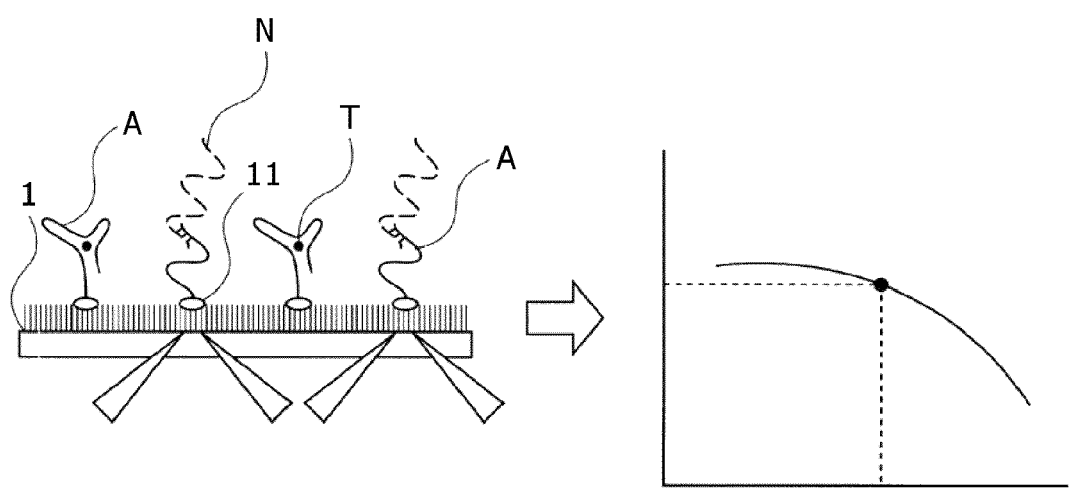
FIG. 6 is a schematic diagram illustrating the fourth step in the first preferred embodiment of the method pertaining to the embodiment.

The following is a step-by-step description of the first embodiment. It is to be noted that FIG. 2 is a flow chart for the method pertaining to the first invention, and FIGS. 3 to 6 are schematic diagrams illustrating each step in the method pertaining to the present embodiment. In addition, there are shown in these figures the sensor's detection surface 1 and the linker 11.

The first step is to introduce a prescribed amount of aptamer A to be immobilized onto the detection surface 1. The aptamer A has terminal functional groups for immobilization onto the detection surface 1. The immobilization onto the detection surface 1 takes place by linkage through the linker 11 (see FIG. 3 for the first step).

The next step is to introduce a sample containing the target substance T and the nucleic acid strand N to the detection surface 1 on which the aptamer A has been immobilized. With both binding competitively with the aptamer A, at least either of the physical change and the chemical change resulting from the aptamer A binding with the nucleic acid strand N is detected (see FIG. 4 for the second step).

The amount of the target substance T in the sample is estimated from the calibration curve to be prepared in the following manner. The detection surface 1, with the aptamer A immobilized thereon, is provided with a prescribed amount of the target substance T and a prescribed amount of the nucleic acid strand N so that they bind competitively with the aptamer A. In this condition, the binding of the aptamer A with the nucleic acid strand brings about the physical change and the chemical change at least either of which is detected. This procedure for detection is repeated with the amount of the nucleic acid strand N kept constant and the amount of the target substance T varied, so that the result of detection is related with the amount of the target substance T introduced. Thus, there is obtained the calibration curve (see FIG. 5 for the third step).

The relationship obtained in the third step mentioned above permits one to estimate the amount of the target substance T in the sample from the result of detection in the second step mentioned above (see FIG. 6 for the fourth step).

The following is a detailed description of the first embodiment.

The method according to the embodiment is not specifically restricted in the object for detection, which is at least either the physical change and the chemical change which result from the aptamer A binding with the nucleic acid strand N. Typical examples of the physical change include the changes in permittivity and mass. Typical examples of the chemical change include the change in structure of the aptamer A and the change in bond strength of the intramolecular bond of the aptamer A.

According to the embodiment, either of the physical change and the chemical change that result from the aptamer A binding with the nucleic acid strand N should preferably be detected by means of the sensor which has the aptamer A immobilized on its detection surface 1 and which permits either of the physical change and the chemical change to take place as the result of the aptamer A binding with the nucleic acid strand N. The means for detection is not restricted to that used in this embodiment. The foregoing manner is desirable because it does not need to modify the aptamer A and the nucleic acid strand N with an unstable label such as dyes. It is also desirable because it permits repeated measurements so long as the detection surface 1 is regenerated.

As mentioned above, a sensor is used to detect either of the physical change and the chemical change that result from the aptamer A binding with the nucleic acid strand N. This sensor is not specially restricted so long as it is capable of detecting either of the physical change and the chemical change that result from the immobilized aptamer A binding with the nucleic acid strand N. Its typical examples include one which is based on the principle of Surface Plasmon Resonance (SPR for short hereinafter) and one which is based on the principle of Quartz Crystal Microbalance (QCM for short hereinafter).

Detection based on the principle of SPR resorts to the change in permittivity which occurs when the aptamer A (immobilized on the detection surface 1) binds with the nucleic acid strand N. To be specific, permittivity changes when the aptamer A (immobilized on the detection surface 1) binds with the nucleic acid strand N, and this change in permittivity is observed in terms of the change in attenuation peak angle of the intensity of reflected light which is due to the surface plasmon resonance. Consequently, the detection based on the principle of SPR varies in sensitivity depending on the amount of the change in permittivity resulting from the aptamer A binding with the nucleic acid strand N.

Detection based on the principle of QCM resorts to the change in mass which occurs when the aptamer A (immobilized on the detection surface 1) binds with the nucleic acid strand N. To be specific, mass changes when the aptamer A (immobilized on the detection surface 1) binds with the nucleic acid strand N, and this change in mass is observed in terms of the change in resonance frequency which is due to the piezoelectric effect of quartz oscillator. Consequently, the detection based on the principle of QCM varies in sensitivity depending on the amount of the change in mass resulting from the aptamer A binding with the nucleic acid strand N.

The target substance T to be determined by the method according to the embodiment is not specifically restricted. It includes, for example, proteins, nucleic acids, hormones, environmental hormones, and drugs. Preferable among these examples are hormones, environmental hormones, and drugs in the form of low-molecular weight compound. Hormones, environmental hormones, and drugs with a low-molecular weight are not usually determined with a high sensitivity on account of the small change in permittivity or mass in direct detection by means of biosensors such as SPR sensor and QCM sensor. Even in this case, low-molecular weight compounds such as hormones, environmental hormones, and drugs can be detected with a high sensitivity by the method according to the present invention.

The aptamer A used in the method according to the embodiment is a molecule (such as nucleic acid) which binds specifically with the target substance T. It is not specially restricted so long as it binds specifically with the target substance T. It includes DNA aptamer, RNA aptamer, peptide aptamer, PNA (peptide nucleic acid) and the like.

The method according to the embodiment is designed to detect at least either of the physical change and the chemical change that result from the aptamer A binding with the nucleic acid strand N; therefore, it can reduce noise due to self-annealed aptamer A. This permits improvement in detection sensitivity without noise increase by increasing the amount of the aptamer A in the method of the embodiment.

According to the embodiment, the aptamer A is immobilized on the detection surface 1 in any way without special restrictions. There are several ways of immobilization as listed below. Immobilization through the avidin-biotin linkage which results from reaction between avidin to modify the terminal groups of the aptamer A and biotin to modify the detection surface 1. Immobilization through the amido linkage which results from reaction between the aminated terminal groups of the aptamer A and carboxylic acid to modify the detection surface 1. Immobilization through the thiol-metal linkage which results from reaction between the thiolized terminal groups of the aptamer A and noble metal constituting the detection surface 1. Immobilization through the physical adsorption of protein which results from reaction between protein to modify the terminal groups of the aptamer A and the detection surface 1 made of a material to readily adsorb protein.

The method of the embodiment does not impose any restrictions on the amount of the aptamer A, which may be properly established in response to the kind and concentration of the target substance T to be determined. The amount of the aptamer A to be immobilized on the detection surface 1 is not specially restricted.

The nucleic acid strand N used in the method of the embodiment is one which has a base sequence complementary to at least a portion of the aptamer A, so that the nucleic acid strand N binds with the aptamer A to bring about the physical change and the chemical change at least either of which is detected for determination of the target substance T.

The nucleic acid strand N is not specially restricted in the number of bases in the base sequence complementary to the aptamer A. Variation in the number of bases in the complementary base sequence leads to variation in the equilibrium constant of the double strand bond between the aptamer A and the nucleic acid strand N. This permits adjustment of sensitivity.

The nucleic acid strand N is not specially restricted in the base sequence complementary to the aptamer A. If the aptamer A has the stem loop structure, the nucleic acid strand N should preferably have the base sequence complementary to the base sequence of the non-stem portion of the aptamer A, so that it effectively binds with the aptamer A, starting from the non-stem part of the self-annealed aptamer A. This leads to improved sensitivity.

Figure 8:
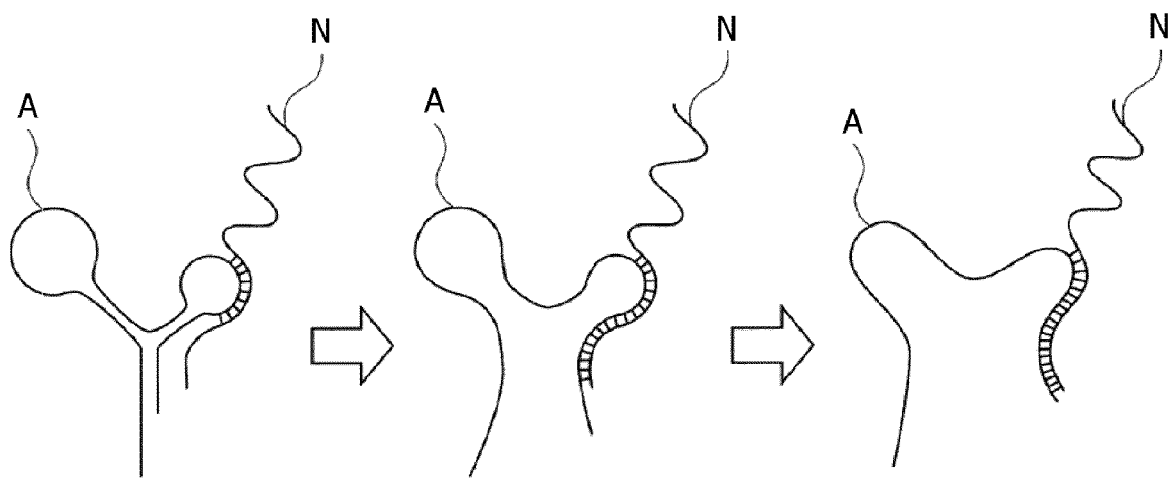
FIG. 8 is a schematic diagram illustrating another example of the preferred nucleic acid strand used in the method pertaining to the embodiment.

In other words, there is an instance in which the self-annealed aptamer A (which has the stem loop structure) does not bind with the target substance T and hence does not contribute to detection. The aptamer A like this causes noise at the time of detection. In this case, the nucleic acid strand N having the base sequence complementary to the base sequence of the non-stem part of the aptamer A loosens the self-annealing of the self-annealed aptamer A having the stem loop structure, thereby contributing detection. Moreover, it also reduces the self-annealed aptamer A, thereby reducing noise and improving detection sensitivity (see FIG. 8).

In the case where the nucleic acid strand N has the base sequence complementary to the base sequence of the non-stem part of the aptamer A, the base sequence complementary to the base sequence of the non-stem part of the aptamer A is not specially restricted in the number of bases; however, the desirable number is no smaller than four. This condition is necessary for the nucleic acid strand N to efficiently bind with the non-stem part of the aptamer A.

Figure 7:
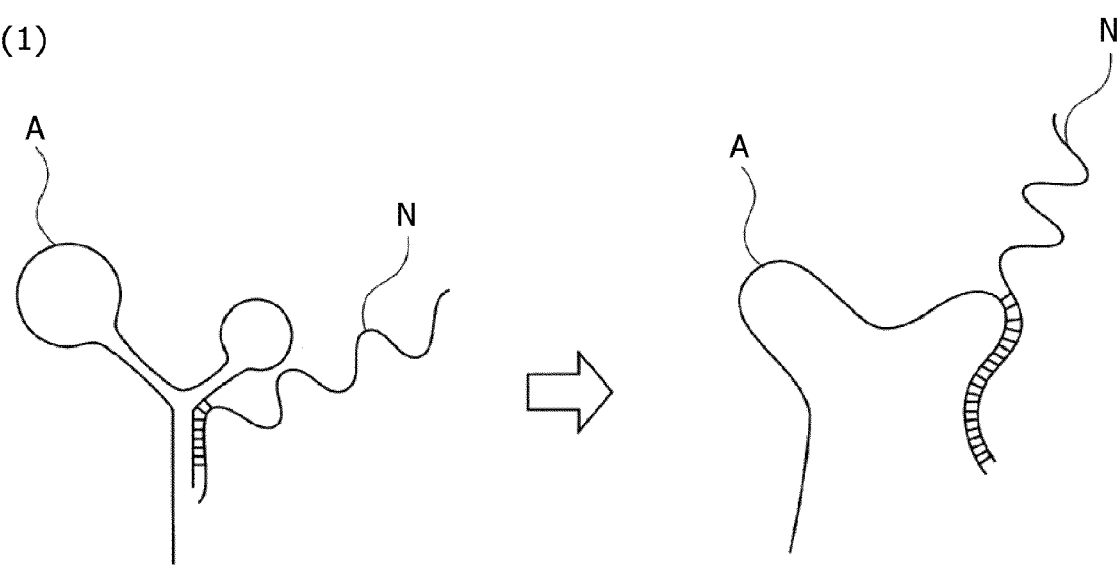
FIG. 7 is a schematic diagram illustrating one example of the preferred nucleic acid strand used in the method pertaining to the embodiment.
Figure 7:
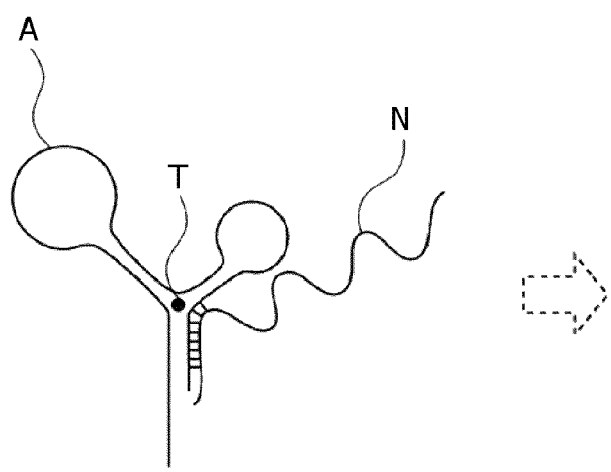

In addition, the nucleic acid strand N should preferably have the base sequence complementary to that part of the base sequence (among the base sequences of the aptamer A) on which the target substance T acts most strongly when it binds with the target substance T. That part of the base sequence of the aptamer A which binds with the target substance T becomes stabilized upon binding with the target substance T. Therefore, the nucleic acid strand N having the base sequence complementary to that part readily binds with the aptamer A which does not yet binds with the target substance T (see FIG. 7(1)) but hardly binds with the aptamer A which has once bound with the target substance T (see FIG. 7(2)).

In the case where the nucleic acid strand N has the base sequence complementary to that part of the base sequence of the aptamer A which binds with the target substance T, the base sequence complementary to that part of the aptamer A which binds with the target substance T is not specially restricted in the number of bases.

In addition, the nucleic acid strand N to be used in the method according to the embodiment is not specially restricted so long as it has a base sequence complementary to at least a portion of the aptamer A. However, it should preferably be one which has a base sequence non-complementary to the aptamer A. The nucleic acid strand N having a base sequence non-complementary to the aptamer A results in a large change in permittivity and mass when it binds with the aptamer A. This leads to improvement in sensitivity.

Moreover, for the nucleic acid strand to result in a large change in permittivity and mass for improved sensitivity upon binding with the aptamer A, at least either of the aptamer A and the nucleic acid strand N may be modified with a substituent which increases at least either of the physical change and the chemical change which occur when the aptamer A binds with the nucleic acid strand N. This substituent is not specially restricted but may be properly selected according to the means for detection. For example, in the case where the aptamer A is immobilized on the surface of the sensor which performs detection based on the principle of SPR, the nucleic acid strand may have its terminal group modified with a dielectric material.

The method according to the present invention is not specially restricted in the amount of the nucleic acid strand N, which may be properly established in response to the structure of the aptamer A and the nucleic acid strand N and the amount of the target substance T to be introduced.

When the aptamer A is allowed to bind competitively with the target substance T and the nucleic acid strand N according to the method of the embodiment, no special restrictions are imposed on the order of introducing the target substance T and the nucleic acid strand N. For example, it is possible to introduce the target substance T and the nucleic acid strand N at the same time. Also, when at least either of the physical change and the chemical change resulting from the aptamer A binding with the nucleic acid strand N is detected by means of the sensor, the target substance T may be introduced prior to the nucleic acid strand N, so that signals can be obtained rapidly before equilibrium is reached in the binding of the aptamer A with the nucleic acid strand N.

Figure 9:
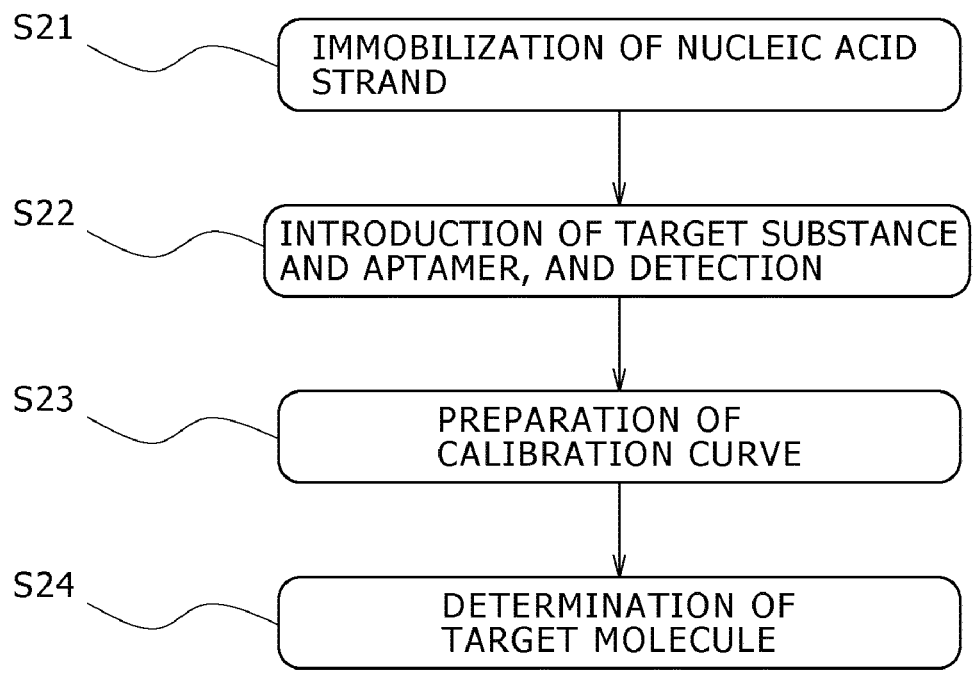
FIG. 9 is a flow chart for the second preferred embodiment of the method pertaining to the embodiment.
Figure 10:
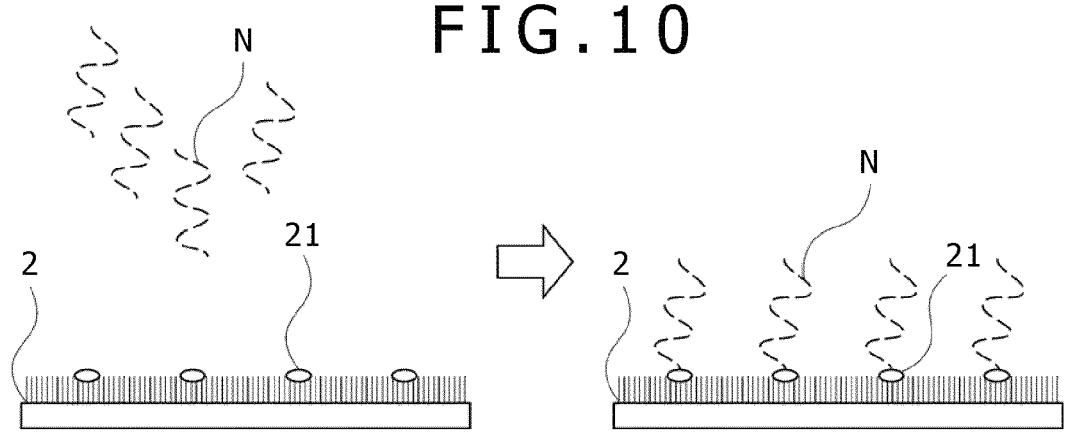
FIG. 10 is a schematic diagram illustrating the first step in the second preferred embodiment of the method pertaining to the embodiment.
Figure 11:
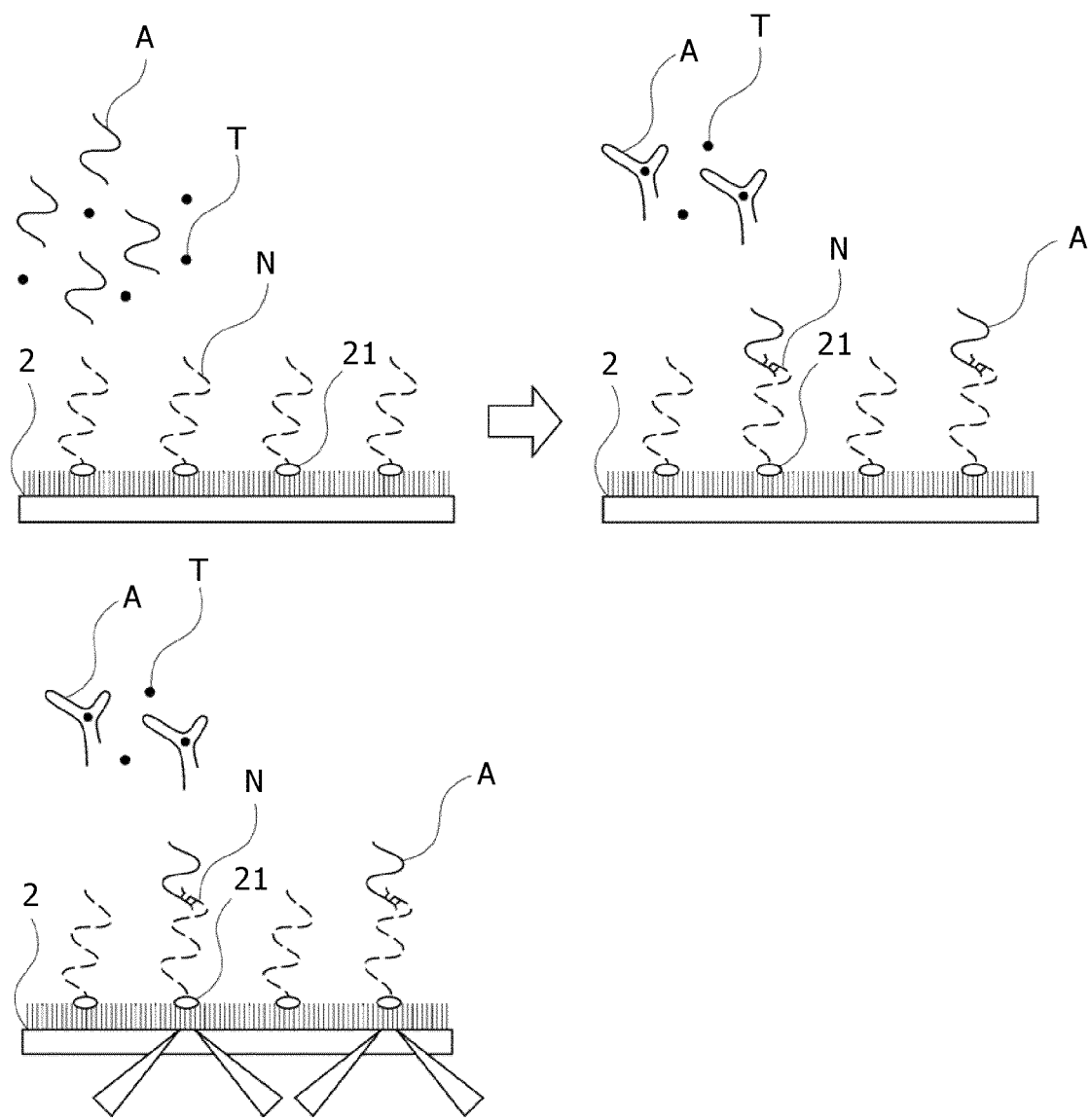
FIG. 11 is a schematic diagram illustrating the second step in the second preferred embodiment of the method pertaining to the embodiment.
Figure 12:
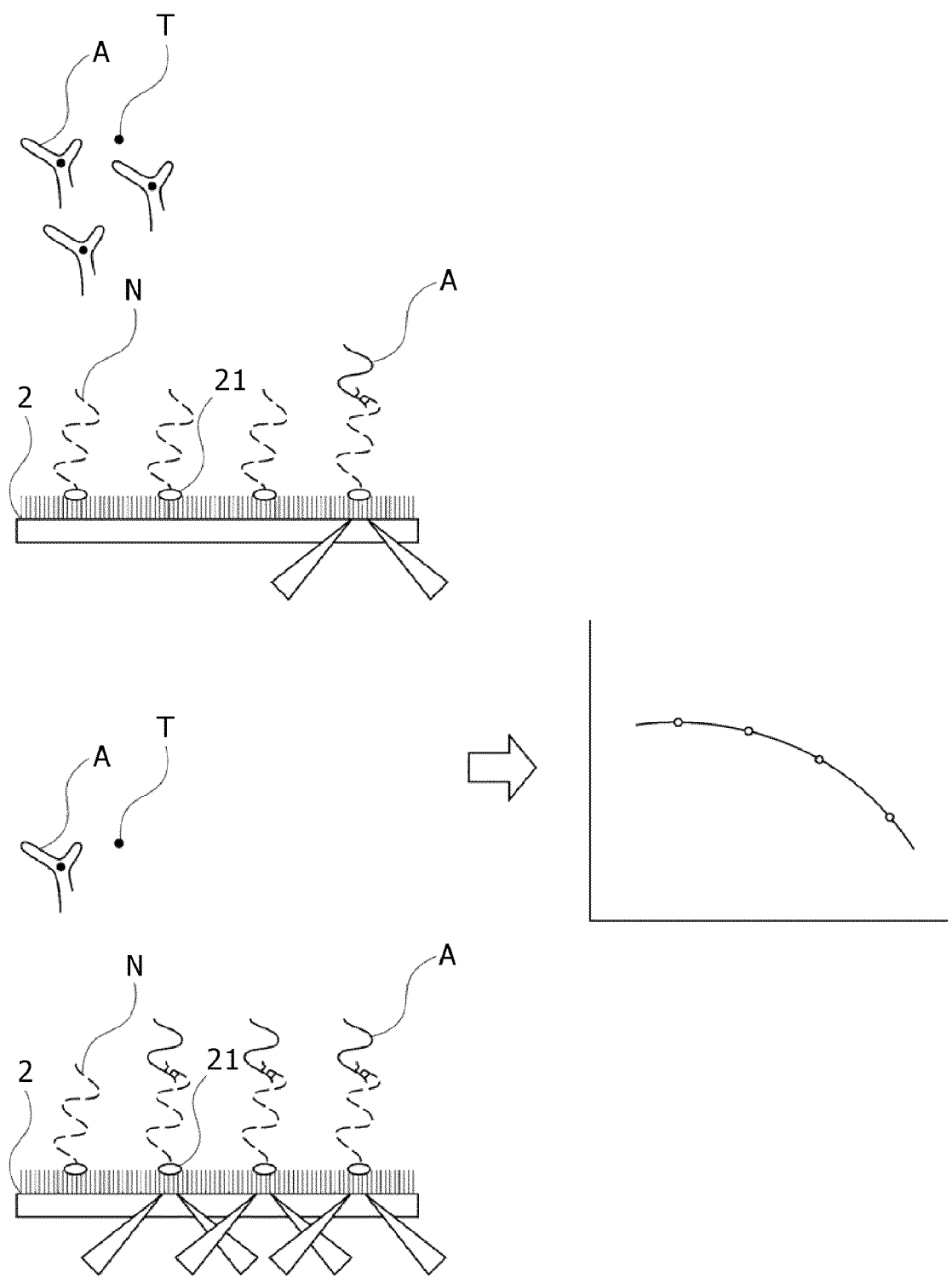
FIG. 12 is a schematic diagram illustrating the third step in the second preferred embodiment of the method pertaining to the embodiment.
Figure 13:
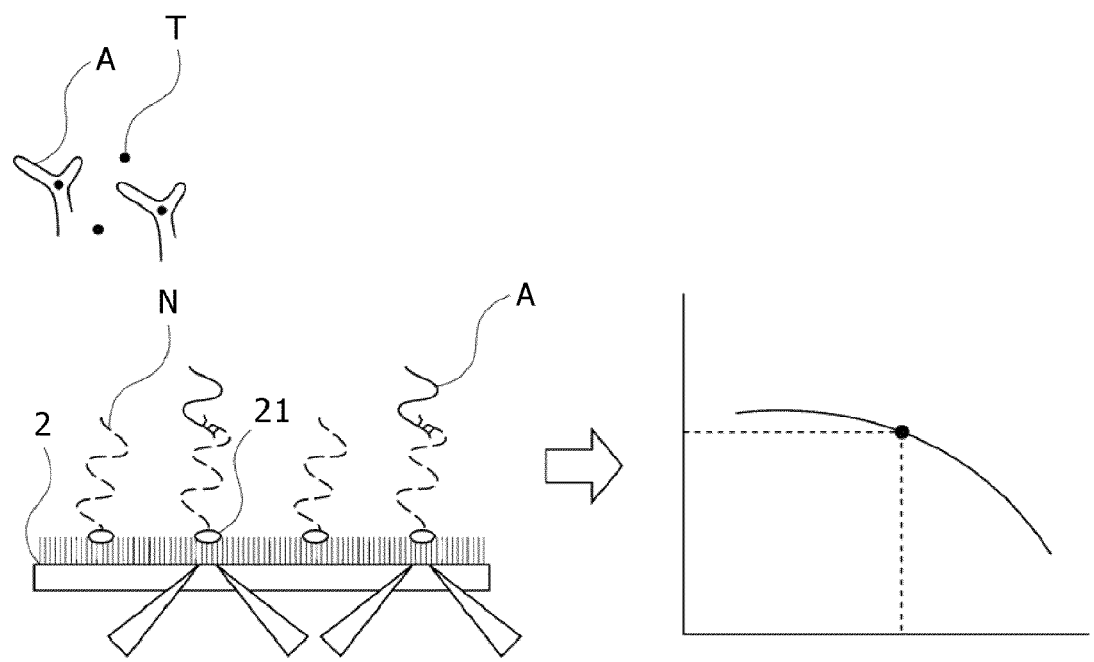
FIG. 13 is a schematic diagram illustrating the fourth step in the second preferred embodiment of the method pertaining to the embodiment.

The following is a step-by-step description of the second embodiment of the embodiment. It excludes those items identical with those in the first embodiment but it mentions only those items different from those in the first embodiment. It is to be noted that FIG. 9 is a flow chart for the second embodiment, and FIGS. 10 to 13 are schematic diagrams illustrating each step in the method pertaining to the embodiment. In addition, there are shown in these figures the sensor's detection surface 2 and the linker 21.

The first step is to introduce a prescribed amount of the nucleic acid strand N to be immobilized onto the detection surface 2. The nucleic acid strand N has terminal functional groups for immobilization onto the detection surface 2. The immobilization onto the detection surface 2 takes place by linkage through the linker 21 (see FIG. 10 for the first step).

The next step is to introduce a sample containing the target substance T and the aptamer A to the detection surface 2 on which the nucleic acid strand N has been immobilized. With the nucleic acid strand N and the target substance T binding competitively with the aptamer A, at least either of the physical change and the chemical change resulting from the nucleic acid strand N binding with the aptamer A is detected (see FIG. 11 for the second step).

The amount of the target substance T in the sample is estimated from the calibration curve to be prepared in the following manner. The detection surface 2, with the nucleic acid strand N immobilized thereon, is provided with a prescribed amount of the aptamer A and a prescribed amount of the target substance T so that they bind competitively with the nucleic acid strand N. In this condition, the binding of the nucleic acid strand N with the aptamer A brings about the physical change and the chemical change, at least either of which is detected. This procedure for detection is repeated with the amount of the aptamer A kept constant and the amount of the target substance T varied, so that the result of detection is related with the amount of the target substance T introduced. Thus, there is obtained the calibration curve (see FIG. 12 for the third step).

The relationship obtained in the third step mentioned above permits one to estimate the amount of the target substance T in the sample from the result of detection in the second step mentioned above (see FIG. 13 for the fourth step).

The following is a detailed description of the second embodiment.

According to this embodiment, the nucleic acid strand N is immobilized on the detection surface 2 of the sensor and the nucleic acid strand N binds with the aptamer A to bring about the physical change and the chemical change, at least either of which is detected by the sensor. Detection in this manner is desirable because it does not need to modify the aptamer A and the nucleic acid strand N with an unstable label such as dyes. It is also desirable because it permits repeated measurements so long as the detection surface 2 is regenerated.

As mentioned above, a sensor is used to detect either of the physical change and the chemical change that result from the nucleic acid strand N binding with the aptamer A. This sensor is not specially restricted so long as it is capable of detecting either of the physical change and the chemical change that result from the nucleic acid strand N binding with the aptamer A. Its typical examples include those which are based on the principles of SPR and QCM.

Detection based on the principle of SPR resorts to the change in permittivity which occurs when the nucleic acid strand N (immobilized on the detection surface 2) binds with the aptamer A. To be specific, permittivity changes when the nucleic acid strand N (immobilized on the detection surface 2) binds with the aptamer A, and this change in permittivity is observed in terms of the change in attenuation peak angle of the intensity of reflected light which is due to the surface plasmon resonance. Consequently, the detection based on the principle of SPR varies in sensitivity depending on the amount of the change in permittivity resulting from the nucleic acid strand N binding with the aptamer A.

Detection based on the principle of QCM resorts to the change in mass which occurs when the nucleic acid strand N (immobilized on the detection surface 2) binds with the aptamer A. To be specific, mass changes when the nucleic acid strand N (immobilized on the detection surface 2) binds with the aptamer A, and this change in mass is observed in terms of the change in resonance frequency which is due to the piezoelectric effect of quartz oscillator. Consequently, the detection based on the principle of QCM varies in sensitivity depending on the amount of the change in mass resulting from the nucleic acid strand N binding with the aptamer A.

The nucleic acid strand N is immobilized on the detection surface 2 in any way without special restrictions. There are several ways of immobilization as listed below. Immobilization through the avidin-biotin linkage which results from reaction between avidin to modify the terminal groups of the nucleic acid strand N and biotin to modify the detection surface 2. Immobilization through the amido linkage which results from reaction between the aminated terminal groups of the nucleic acid strand N and carboxylic acid to modify the detection surface 2. Immobilization through the thiol-metal linkage which results from reaction between the thiolized terminal groups of the nucleic acid strand N and noble metal constituting the detection surface 2. Immobilization through the physical adsorption of protein which results from reaction between protein to modify the terminal groups of the nucleic acid strand N and the detection surface made of a material to readily adsorb protein.

The method does not impose any restrictions on the amount of the aptamer A, which may be properly established in response to the kind and concentration of the target substance T to be determined. It is possible to alter the dynamic range for the target substance T by varying the concentration of the aptamer A.

Moreover, for the aptamer A to result in a large change in permittivity and mass for improved sensitivity upon binding with the nucleic acid strand, at least either of the aptamer A and the nucleic acid strand N may be modified with a substituent which increases at least either of the physical change and the chemical change which occur when the aptamer A binds with the nucleic acid strand N. This substituent is not specially restricted but may be properly selected according to the means for detection. For example, in the case where the nucleic acid strand N is immobilized on the surface of the sensor which performs detection based on the principle of SPR, the aptamer A may have its terminal group modified with a dielectric material.

The method according to the present embodiment is not specially restricted in the amount of the nucleic acid strand N (to be immobilized on the detection surface 2 of the sensor), which may be properly established in response to the structure of the aptamer A and the nucleic acid strand N and the amount of the target substance T to be introduced.

According to this embodiment, no special restrictions are imposed on the order of introducing the target substance T and the aptamer A onto the detection surface 2. For example, it is possible to introduce the target substance T and the aptamer A at the same time. It is also possible to previously react the target substance T with the aptamer A and then introducing the reaction product into the nucleic acid strand N, so that detection is accomplished in such a state that an equilibrium of reaction has been reached between the target substance T and the aptamer A. This permits the highly sensitive determination of the target substance T.

Figure 14:
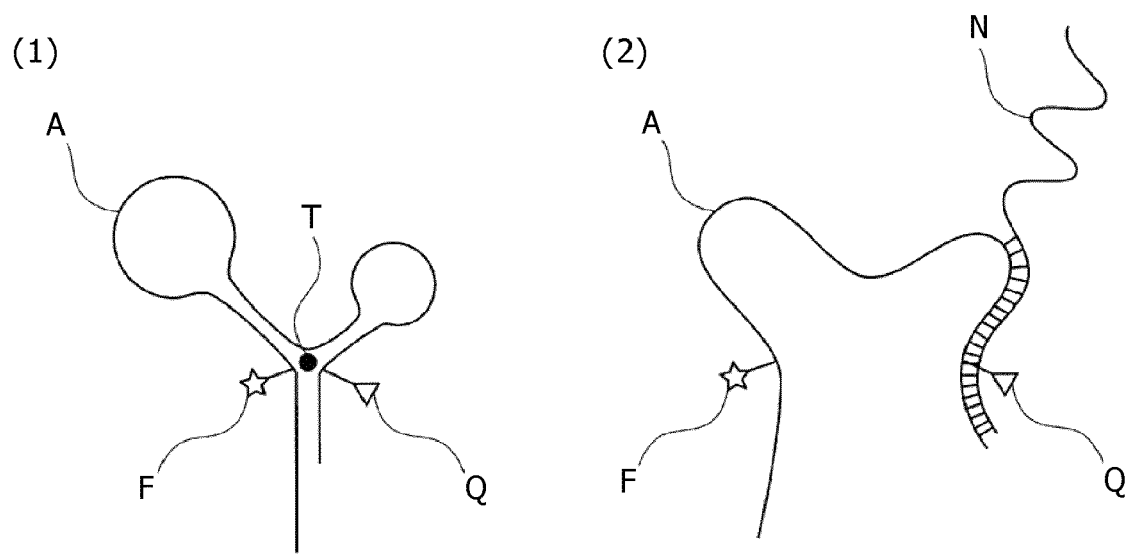
FIG. 14 is a schematic diagram illustrating the third preferred embodiment for the method pertaining to the embodiment.

The following is a description of the third embodiment. It excludes those items identical with those in the first and second embodiments but it mentions only those items different from those in the first and second embodiments. FIG. 14 is a schematic diagram for the third embodiment, in which "F" denotes a fluorescent dye and "Q" denotes a quencher that quenches the fluorescent dye Q.

According to this embodiment, the aptamer A binds with the nucleic acid strand N to bring about the physical change and the chemical change at least either of which is detected by means of the fluorescent dye F and the quencher Q that quenches the fluorescent dye F, both modifying the base sequence of the aptamer A. The fluorescent dye F and the quencher Q modify the aptamer A in such a way that they are close to each other when the aptamer A is connected to the target substance T or in the self-annealed state but they are away from each other when the aptamer A is connected with the nucleic acid strand N (see FIG. 14).

When the aptamer A is connected to the target substance T or in the self-annealed state, the fluorescent dye F is close to the quencher Q and the fluorescent dye F is quenched by the quencher Q, so that no fluorescence is observed (see FIG. 14(1)).

By contrast, when the aptamer A is connected to the nucleic acid strand N, the fluorescent dye F is away from the quencher Q and the fluorescent dye F is not quenched by the quencher Q, so that fluorescence is observed (see FIG. 14(2)).

Therefore, according to the method of this embodiment, the change in structure which results from the aptamer A binding with the nucleic acid strand N can be observed in terms of the change in the intensity of fluorescence of the fluorescent dye F that modifies the aptamer A.

The method pertaining to the present embodiment offers the advantage that the target substance T can be determined with a high sensitivity even in the case where it is a low-molecular one and hence does not permit sensitive detection for either of the physical change and the chemical change that result from the aptamer A binding with the target substance T.

In addition, the foregoing method is free of effect produced by the self-annealing of the aptamer A and hence is capable of reducing noise due to the self-annealed aptamer A.

Moreover, the foregoing method permits the calculation of the equilibrium constant for the aptamer a and the target substance T from the equilibrium state of the nucleic acid strand N and the aptamer A and the equilibrium state of the nucleic acid strand N, the target substance t, and the aptamer A.

Furthermore, it is possible to easily measure the affinity of the target substance t with the aptamer a, if the amount of the target substance t is varied, with the amount of the aptamer a kept constant. Therefore, the method can be easily used for the screening of drugs, for example.

EXAMPLES

The embodiments will be described in more detail with reference to the following examples.

<Conditions of Experiments>

The reference substance was methyl cholate, and the aptamer was one prepared for cholic acid. The 5'-end was modified with biotin for binding with the detection surface. Table 1 shows the base sequence of the aptamer and the reference DNA.

TABLE 1

| | Base sequence |
|---|---|
| Aptamer | 5'-GCAGGGTCAATGGAATTAATGATCAATTG ACAG<u>ACGCAAGTCTCCTGC</u>-3' (sequence number 1) |
| Reference DNA | 5'-TCTTGAGTCGGAAGCCAAGCAAACTAAGA GAACATGATGTTCTCAGGTCA-3' (sequence number 2) |

* The underline denotes the portion complementary to the nucleic acid strand shown below.

The competitive molecule for the target substance was nucleic acid strand (20 Mer in length) having the base sequence complementary to one portion of the aptamer. The base sequence is such that the complementary portion is 15 mer (nucleic acid strand 1) and 10 mer (nucleic acid strand 2) from the 5'-end and the remainder does not bind non-specifically with the aptamer and the nucleic acid strand itself. Table 2 shows each nucleic acid strand.

TABLE 2

| | Base sequence |
|---|---|
| 15 mer (nucleic acid strand 1) | 5'-<u>GCAGGAGACTTGCGC</u>GACAG-3' (sequence number 3) |
| 10 mer (nucleic acid strand 2) | 5'-<u>GCAGGAGACT</u>ACGCAGACAG-3' (sequence number 4) |

* The underline denotes the portion complementary to the aptamer.

The running buffer (pH 7.6) was prepared from 50 mM Tris-HCl, 300 mM NaCl, 30 mM KCl, and 5 mM MgCl2. SPR measurement was accomplished by using BIACOREX, made by Biacore Inc.

The foregoing running buffer was used as a solvent for various solutions in experiments unless otherwise stated.

<Method for Immobilization of Aptamer>

The aptamer was immobilized on the SA chip (made by Biacore Inc.) in the following manner. The SA chip has its gold surface modified with dextran having carboxyl groups, and the carboxyl groups have streptoavidin immobilized thereon. The SA chip was cleaned with an aqueous solution of 50 mM NaOH. The SA chip was given 10 μM of biotin-modified aptamer which was fed at a rate of 5 μL/min for 480 seconds. The SA chip was cleaned again with an aqueous solution of 50 mM NaOH. The aptamer was immobilized to such an extent that it does not react any more. The amount of the immobilized aptamer was about 1500 to 2500 Resonance Unit.

The same procedure as mentioned above was repeated to immobilize the reference DNA on the reference cell except that the aptamer was replaced by the reference DNA.

<Method for Measurement of SPR>

Each sample was prepared by mixing (in a ratio of 1:1) the nucleic acid strand (2 μM) with the methyl cholate in varied concentrations of 0 μM, 0.1 μM, 1 μM, 10 μM, 50 μM, and 100 μM. The thus prepared sample was fed to the aptamer cell and to the reference cell at the same time at a flow rate of 5 μL/min for 480 seconds or 10 μL/min for 300 seconds. In order to eliminate the effect of the acetonitrile as the solvent, blank measurements for correction were carried out for each sample by using the acetonitrile-containing running buffer of the same composition.

During measurement, the cell was washed by feeding with aqueous solutions of 3 mM NaOH and 500 mM of HCl.

<Results of Measurements>

Figure 15:
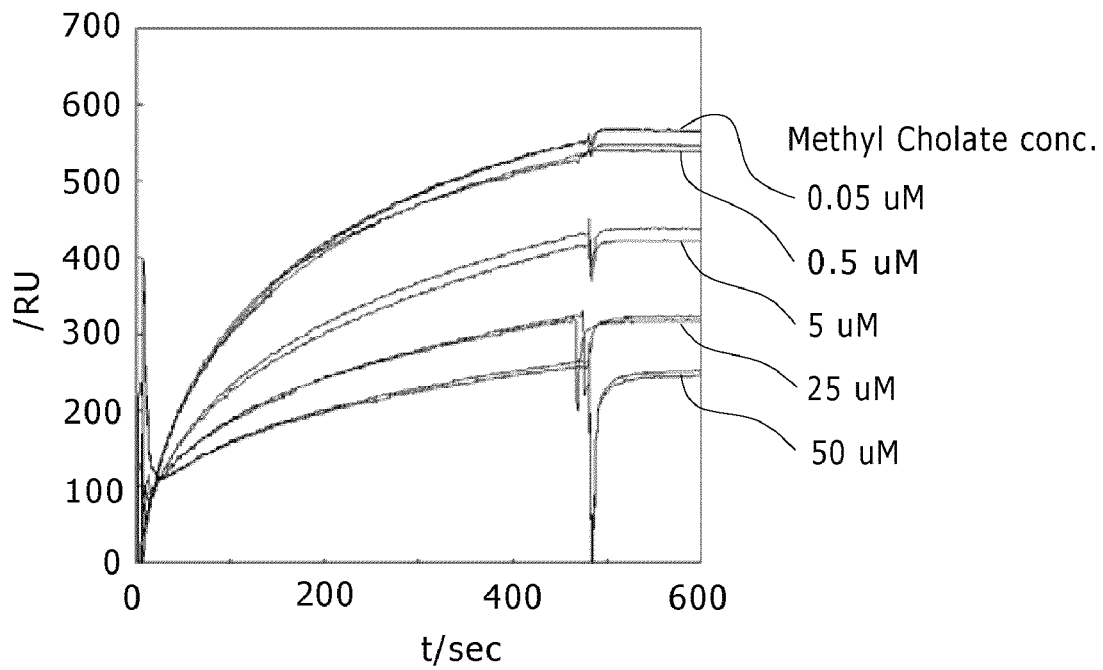
FIG. 15 is a diagram showing the difference in SPR angle shift between the aptamer cell (used in the example of the embodiment) and the reference cell.
Figure 15:
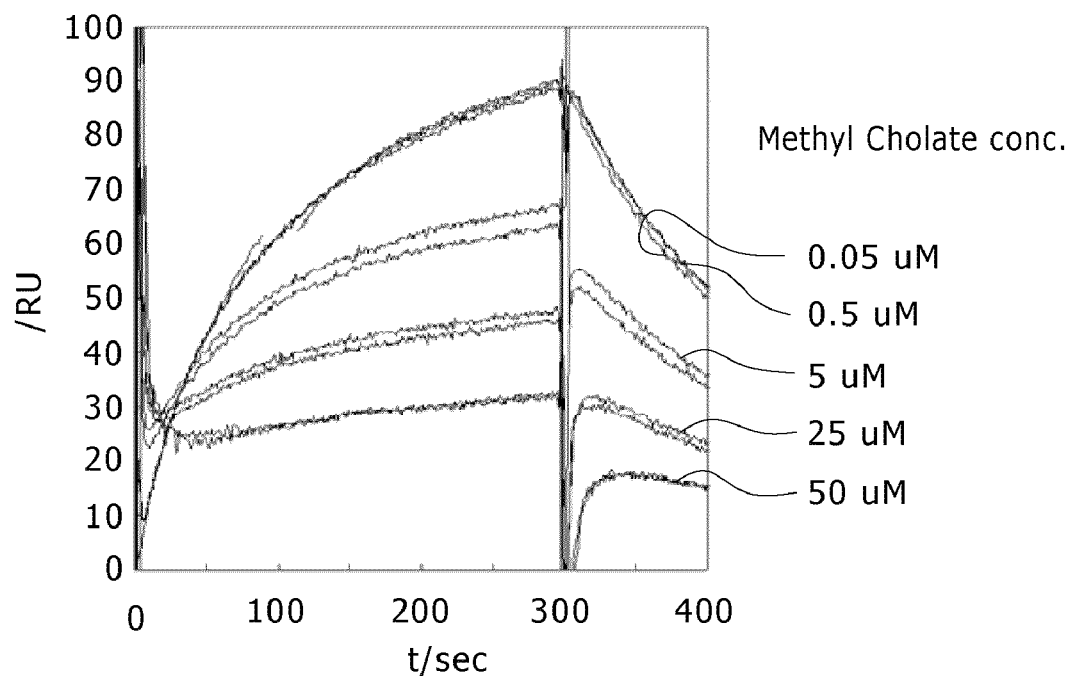

FIG. 15 shows the difference of SPR angle shift between the aptamer cell and the reference cell for the nucleic acid strand 1 (5 μL/min) and the nucleic acid strand 2 (10 μL/min). It is noted that the signal intensity increases while the sample is being fed, indicating the binding of the nucleic acid strand with the substrate surface. By contrast, after the feeding of the sample has been completed and the feeding of the running buffer has been started, the signal intensity decreases, indicating the dissociation of the nucleic acid strand. In the case of the nucleic acid strand 1, the signal intensity decreases more slowly after the completion of the sample feeding. This suggests a slow rate of dissociation from the aptamer. The foregoing results of measurements indicate the capability of detecting the change in permittivity which results from the aptamer binding with the nucleic acid strand.

Figure 16:
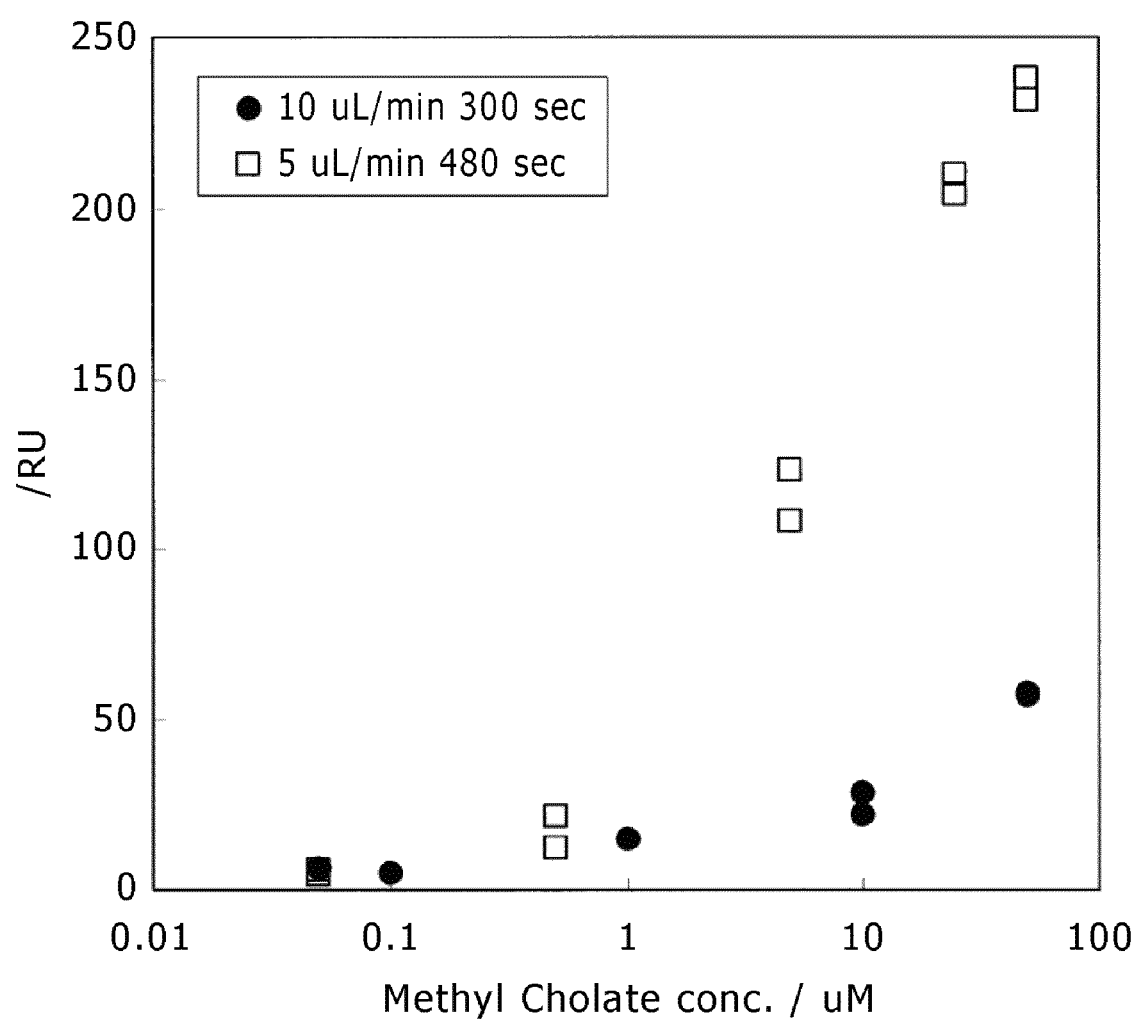
FIG. 16 is a diagram in which is plotted the difference between the peak shift value at each methyl cholate concentration (in the example of the embodiment) and the peak shift value of blank.

FIG. 16 shows the value obtained by subtracting the peak shift value (at each methyl cholate concentration) from the peak shift value in blank test, in the case of the nucleic acid strand 1. There was obtained the peak shift value which is dependent on the concentration of methyl cholate. It was found that the signal intensity tends to increase as the feeding time increases and the reaction proceeds accordingly. The method according to the present invention gave the maximum detection limit of 0.5 μM for methyl cholate. It was capable of highly sensitive detection of the target substance.

The present embodiment provides a method for highly sensitive determination of a target substance with the help of an aptamer.

It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

The invention claimed is:

1. A method for determination of a target substance, said method comprising:

causing an aptamer with a stem loop structure capable of specific binding with a target substance to bind competitively with said target substance and a nucleic acid strand having a base sequence complementary to a non-stem portion of said aptamer;

detecting at least either of the physical change and the chemical change that results from said aptamer binding with said nucleic acid strand;

and determining said target substance based on the detection of said aptamer binding with said nucleic acid strand;

and where said aptamer is immobilized on the detection surface of a sensor which performs detection based on at least surface plasmon resonance and which is capable of detecting the change in permittivity that results from said aptamer binding with said nucleic acid strand.

2. The method as defined in claim 1, wherein said sensor is one which performs detection based on the principle of quartz crystal microbalance and which is capable of detecting the change in mass that results from said aptamer binding with said nucleic acid strand.

3. The method as defined in claim 1, wherein said nucleic acid strand is one which has a base sequence non-complementary to at least another portion of said aptamer.

4. The method as defined in claim 1, wherein at least either of said aptamer and said nucleic acid strand is one which is modified with a substituent that increases either of the physical change and the chemical change which results from said aptamer binding with said nucleic acid strand.

5. The method as defined in claim 1, wherein said nucleic acid strand is one which is immobilized on the detection surface of the sensor.

6. The method as defined in claim 5, wherein said sensor performs detection based on surface plasmon resonance in such a way that said sensor detects the change in permittivity that results from said nucleic acid strand binding with said aptamer.

7. The method as defined in claim 5, wherein said sensor performs detection based on the principle of quartz oscillator microbalance in such a way that said sensor detects the change in mass that results from said nucleic acid strand binding with said aptamer.

8. A method for determination of a target substance in a sample, said method comprising:

immobilizing an aptamer with a stem loop structure capable of specifically binding with said target substance on the detection surface of a sensor;

detecting at least one of a physical change and a chemical change which results from said aptamer binding with a nucleic acid strand, with said aptamer competitively binding with said target substance in said sample and the nucleic acid strand having a base sequence complementary to a non-stem portion of said aptamer;

detecting at least one of the physical change including at least one of a change in permittivity and a change in aptamer and the chemical change which results from said aptamer binding with said nucleic acid strand, with said aptamer competitively binding with a prescribed amount of said target substance and a prescribed amount of said nucleic acid strand, thereby knowing the relationship between the amount of said target substance and the result of detection; and estimating the amount of said target substance in said sample.

9. The method as defined in claim 8, wherein the amount of said target substance in said sample is estimated from a calibration curve of known amounts of said target substance and said nucleic acid strand.

10. The method as defined in claim 8, wherein the chemical change includes at least one of a change in structure of said aptamer and a change in bond strength of an intra-molecular bond of said aptamer.

11. A method for determination of a target substance, said method comprising:

causing an aptamer with a stem loop structure capable of specific binding with a target substance to bind competitively with said target substance and a nucleic acid strand having a base sequence complementary to a non-stem portion of said aptamer;

detecting at least one of a physical change and a chemical change that result from said aptamer binding with said nucleic acid strand using a quencher and a fluorescent dye that both modify the aptamer;

and determining said target substance based on the detection of said aptamer binding with said nucleic acid strand.

* * * * *

SEQUENCE LISTING

<160> NUMBER OF SEQ ID NOS: 4

<210> SEQ ID NO 1
<211> LENGTH: 48
<212> TYPE: DNA
<213> ORGANISM: Artificial sequence
<220> FEATURE:

```
<223> OTHER INFORMATION: Synthesized: aptamer 1

<400> SEQUENCE: 1
gcagggtcaa tggaattaat gatcaattga cagacgcaag tctcctgc            48

<210> SEQ ID NO 2
<211> LENGTH: 50
<212> TYPE: DNA
<213> ORGANISM: Artificial sequence
<220> FEATURE:
<223> OTHER INFORMATION: Synthesized: reference DNA

<400> SEQUENCE: 2
tcttgagtcg gaagccaagc aaactaagag aacatgatgt tctcaggtca           50

<210> SEQ ID NO 3
<211> LENGTH: 20
<212> TYPE: DNA
<213> ORGANISM: Artificial sequence
<220> FEATURE:
<223> OTHER INFORMATION: Synthesized: nucleotide 1

<400> SEQUENCE: 3
gcaggagact tgcgtgacag                                            20

<210> SEQ ID NO 4
<211> LENGTH: 20
<212> TYPE: DNA
<213> ORGANISM: Artificial sequence
<220> FEATURE:
<223> OTHER INFORMATION: Synthesized: nucleotide 2

<400> SEQUENCE: 4
gcaggagact acgcagacag                                            20
```